(12) United States Patent
Fujii et al.

(10) Patent No.: US 11,834,674 B2
(45) Date of Patent: Dec. 5, 2023

(54) MODIFIED IMMUNOCYTE, METHOD FOR PRODUCING MODIFIED IMMUNOCYTE AND UTILIZATION THEREOF

(71) Applicant: RIKEN, Saitama (JP)

(72) Inventors: Shin-ichiro Fujii, Saitama (JP); Kanako Shimizu, Saitama (JP); Satoru Yamasaki, Saitama (JP); Jun Shinga, Saitama (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 15/534,366

(22) PCT Filed: Dec. 11, 2015

(86) PCT No.: PCT/JP2015/084826
§ 371 (c)(1),
(2) Date: Oct. 16, 2017

(87) PCT Pub. No.: WO2016/093350
PCT Pub. Date: Jun. 16, 2016

(65) Prior Publication Data
US 2018/0044631 A1    Feb. 15, 2018

(30) Foreign Application Priority Data
Dec. 11, 2014 (JP) .................. 2014-251336

(51) Int. Cl.
*A61K 35/17* (2015.01)
*C12N 5/0783* (2010.01)
(Continued)

(52) U.S. Cl.
CPC ............ *C12N 5/0636* (2013.01); *A61K 35/17* (2013.01); *A61K 39/39* (2013.01);
(Continued)

(58) Field of Classification Search
CPC ...... C12N 9/22; C12N 2310/20; C12N 15/11; C12N 15/113; C12N 15/111; C12N 2800/80; C12N 15/86; C12N 15/907; C12N 15/102; C12N 2310/321; C12N 2510/00; C12N 15/1138; C12N 15/63; C12N 2750/14143; C12N 15/8213; C12N 15/90; C12N 2310/3521; C12N 15/87; C12N 2310/315; C12N 2310/531; C12N 15/70; C12N 15/8282; C12N 15/902; C12N 2740/15043; C12N 15/1137; C12N 15/74; C12N 15/85; C12N 2320/32; C12N 2740/16043; C12N 15/62; C12N 15/88; C12N 2310/11; C12N 2310/3519; C12N 2330/51; C12N 5/16; C12N 7/00; C12N 9/16; C12N 15/115; C12N 15/746; C12N 15/8201; C12N 15/8218; C12N 15/8509; C12N 2310/122; C12N 2310/13; C12N 2310/141; C12N 2310/31; C12N 2310/32; C12N 2310/33; C12N 2320/11; C12N 2320/31; C12N 2320/33; C12N 2501/515; C12N 2501/599; C12N 5/0647; C12N 9/96; C12N 15/01; C12N 15/09; C12N 15/1031; C12N 15/1034; C12N 15/1082; C12N 15/1086; C12N 15/1093; C12N 15/1135; C12N 15/625; C12N 15/635; C12N 15/64; C12N 15/68; C12N 15/71; C12N 15/743; C12N 15/76; C12N 15/79; C12N 15/81; C12N 15/8202; C12N 15/8203; C12N 15/8205; C12N 15/8207; C12N 15/8238; C12N 15/8241; C12N 15/8261; C12N 15/827; C12N 15/8273; C12N 15/8287; C12N 1/20; C12N 1/205; C12N 2015/8518; C12N 2310/10; C12N 2310/16; C12N 2310/341; C12N 2310/346; C12N 2320/13; C12N 2800/30; C12N 2830/001; C12N 2830/002; C12N 2830/003; C12N 2830/008; C12N 2840/445; A61K 48/00;
(Continued)

(56) References Cited

U.S. PATENT DOCUMENTS

2010/0233215 A1  9/2010  Fujii et al.
2011/0020932 A1  1/2011  Wakao et al.
(Continued)

FOREIGN PATENT DOCUMENTS

JP    2007-217360    8/2007
JP    2013-176403    9/2013
(Continued)

OTHER PUBLICATIONS

Cheng et al., Efficient Activation of Vα14 Invariant NKT Cells by Foreign Lipid Antigen is Associated with Concurrent Dendritic Cell-Specific Self Recognition. J Immunol Mar. 1, 2007, 178 (5) 2755-2762 (Year: 2007).*
(Continued)

*Primary Examiner* — Arthur S Leonard
(74) *Attorney, Agent, or Firm* — CASIMIR JONES, S.C.; Tanya A. Arenson

(57) ABSTRACT

A modified immunocyte: (1) which expresses an exogenous unmodified T cell receptor α-chain and an exogenous T cell receptor β-chain on the cell surface thereof; or (2) which contains a polynucleotide encoding a T cell receptor α-chain and a polynucleotide encoding a T cell receptor β-chain. Thus, a new tool whereby immunity can be appropriately induced in vivo is provided.

12 Claims, 6 Drawing Sheets
Specification includes a Sequence Listing.

(51) Int. Cl.
*A61K 39/39* (2006.01)
*C12N 5/10* (2006.01)
*C07K 14/725* (2006.01)
*C12N 15/09* (2006.01)
*C12N 15/00* (2006.01)

(52) U.S. Cl.
CPC ............ *C07K 14/7051* (2013.01); *C12N 5/10* (2013.01); *C12N 15/00* (2013.01); *C12N 15/09* (2013.01); *C12N 2501/599* (2013.01); *C12N 2510/00* (2013.01)

(58) Field of Classification Search
CPC ............ A61K 48/0058; A61K 48/0041; A61K 48/0091; A01K 2227/105; A01K 2207/12; A01K 67/027; A01K 67/0278; A01K 2217/00; A01K 2217/072; A01K 2217/075; A01K 2217/15; A01K 2267/01; A01K 2267/025; A01K 2267/0306; A01K 67/0271; A01K 67/0275
See application file for complete search history.

(56) References Cited

U.S. PATENT DOCUMENTS

| | | | |
|---|---|---|---|
| 2011/0158954 | A1 | 6/2011 | Ideno et al. |
| 2011/0236362 | A1 | 9/2011 | Watarai et al. |
| 2011/0280895 | A1 | 11/2011 | Fujii et al. |
| 2013/0189302 | A1 | 7/2013 | Fujii et al. |

FOREIGN PATENT DOCUMENTS

| | | |
|---|---|---|
| WO | 2007/097370 | 8/2007 |
| WO | 2016/007570 | 1/2016 |

OTHER PUBLICATIONS

Chodon et al., Adoptive transfer of MART-1 T cell receptor transgenic lymphocytes and dendritic cell vaccination in patients with metastatic melanoma (Clin Cancer Res, 2014, 20:2457-2465) (Year: 2014).*

Van der Veken et al., AB T-Cell Receptor Engineered ;D T Cells Mediate Effective Antileukemic Reactivity (Cancer Res, 2006, 66:3331-3337) (Year: 2006).*

Uldrich et al., CD1d-lipid antigen recognition by the gd TCR (Nature Immunology, 2013, 14:1137-1147) (Year: 2013).*

Birkholz et al., Transfer of mRNA encoding recombinant immunoreceptors reprograms CD4+ and CD8+ T cells for use in the adoptive immunotherapy of cancer. Gene Therapy (2009) 16, 596-604 (Year: 2009).*

Shimizu et al., Transfer of mRNA Encoding Invariant NKT Cell Receptors Imparts Glycolipid Specific Responses to T Cells and γδT Cells (PLoS One, (10)6:e0131477, published on Jun. 29, 2015) (Year: 2015).*

Takahashi, Tsuyoshi et al., Human invariant natural killer T cells . . . 2009, vol. 90, No. 2, pp. 137-142, Abstract, Table 1.

International preliminary report on patentability, International Application No. PCT/JP2015/084826, dated Jun. 13, 2017.

International Search Report, International Application No. PCT/JP2015/084826, dated Feb. 9, 2016.

Smith, Drake J. et al.: "Genetic engineering of hematopoietic . . . ",Proceedings National Academy of SciencesPNAS,vol. 112, No. 5, Feb. 3, 2015 (Feb. 3, 2015), pp. 1523-1528, XP055382016,US ISSN: 0027-8424, DOI:10.1073/pnas.1424877112.

Matangkasombut, P. et al. "Natural killer T cells and the regulation of asthma",Mucosal Immunology; Nature Publishing Group,vol. 2, No. 5,Sep. 1, 2009, pp. 383-392 (Sep. 1, 2009),XP055092762.

Bendelac A et al.: "Increased Interleukin 4 and . . . ",The Journal of Experimental Medicine, Rockefeller University Press, US,vol. 184, No. 4, Jan. 1, 1996 (Jan. 1, 1996), pp. 1285-1293, XP001014592,ISSN: 0022-1007, DOI:10.1084/JEM.184.4.1285 * section "Materials and Methods"*.

Taniguchi, Masaru et. al.: "Essential requirement of an invariant Va14 T cell . . . ", Oct. 1, 1996 (Oct. 1, 1996), pp. 11025-11028, XP55465486, Retrieved from theInternet:URL:http://www.pnas.org/content/pnas/93/20/11025.full.pdf [retrieved on Apr. 9, 2018] * section "Materials and Methods"*.

EP Search Report, EP Patent Application No. 15867608.0, dated Apr. 26, 2018.

Vivier et al., "Targeting natural killer cells and natural killer T cells in cancer" Nature Reviews Immunology, vol. 12 Apr. 2012, 239-252, XP055023835.

Uematsu et al,. "In Transgenic Mice the Introduced Functional T Cell Receptor β Gene Prevents Expression of Endogenous β Genes" Cell, vol. 52, 831-841. Mar. 25, 1988. 1988 by Cell Press, XP023908625.

EP Office Action, EP Patent Application No. 15867608.0, dated Jan. 29, 2019, 5 pages.

Kappes, et al., Surface expression of alternative forms of the TCR/CD3 complex. Proc Natl Acad Sci U S A. Dec. 1, 1991;88(23):10619-23.

Office Action for EP 15867608.0, dated Nov. 18, 2019, 4 pages.

Wang et al., "The structural basis of αβ T-lineage immune recognition: TCR docking topologies, mechanotransduction, and co-receptor function" Immunol Rev. Author manuscript; available in PMC Nov. 2013 01.NIH-PA 2013 vol. 250: 102-119.

Office Action for EP Patent Application No. 15867608.0, dated Sep. 21, 2020, 5 pages.

Van Der Veken, L. et al., AB T-Cell Receptor Engineered yD T Cells Mediate Effective Antileukemic Reactivity, Cancer Research 2006, vol. 66, pp. 3331-3337.

Bunse, M. et al., RNAi-mediated TCR Knowckdown Prevents Autoimmunity in Mice Caused by Mixed TCR Dimers Following TCR Gene Transfer, Molecular Therapy Nov. 2014, vol. 22, pp. 1983-1991.

Office Action for CA Patent Application No. 2,977,606, dated Oct. 26, 2021, 5 pages.

* cited by examiner

NKT cells differentiate in thymus gland, like conventional T cells

Dashtsoodol N et al, Frontiers in Immunology, 2019

Bennstein SB, Frontiers in Immunology, 2018

MODIFIED IMMUNOCYTE, METHOD FOR PRODUCING MODIFIED IMMUNOCYTE AND UTILIZATION THEREOF

TECHNICAL FIELD

The present invention relates to a new tool capable of appropriately inducing the activation of immunity in the immune response in the body.

BACKGROUND ART

Based on the results of previous studies that clarify the classification of immunocytes, the process of maturation, the function of cells, and the like, various immunocytes are used for immunotherapy. Immunotherapy is a therapeutic method of disease, which is not dependent on chemical compounds, by artificially stimulating induction of innate immunity, acquired immunity, or a combination thereof. Therefore, it is expected as a therapeutic method capable of alleviating a physical burden on a patient, which induces a function inherently provided in the body.

In innate immunity, immunocytes involved in innate immunity instantaneously responses foreign substances in the body by pattern recognition, therefore, innate immunity is expected to be effective even for the cases that are not covered by antigen-specific immunocyte therapy. Accordingly, the therapy for improving innate immunity has an advantage capable of being used not only for monotherapy but also for combination therapy for the purpose of supplementing the antigen-specific immunocyte therapy.

As the immunocytes involved in innate immunity, natural killer cells (NK cells), γδ T cells, and natural killer T cells (NKT cells) are known. In the lymphocytes in the body, the proportion of these immunocytes involved in innate immunity is generally low. Therefore, the immunotherapy for enhancing the innate immunity actually adopts the method in which lymphocytes are collected from a subject to be treated, the intended immunocytes are cultured, the number of the cells is increased, and then the cells are returned to the body of the subject to be treated. In a conventional method, however, there were some cases that the intended immunocytes did not proliferate and were not activated as desired, and these depends on the state of the lymphocytes collected from a subject to be treated.

In view of such problems, the present inventors are involved in the establishment of a method for utilizing the cells in which cells are amplified by passing through initialized cells such as iPS cells from patient-derived NKT cells and then the cells are redifferentiated to NKT cells (Patent Literatures 1 and 2).

CITATION LIST

Patent Literature

Patent Literature 1: WO 2008/038579 (published on Apr. 3, 2008)
Patent Literature 2: WO 2010/027094 (published on Mar. 11, 2010)

SUMMARY OF INVENTION

Technical Problem

As a result of investigating various approaches to enhance innate immunity in the body, the present inventors concluded that it is required to prepare novel immunocyte having an excellent functional capability to activate innate immunity easily and effectively and to improve the cell proliferation, rather than proliferating and activating the cells themselves involved in innate immunity.

In view of the above investigation, an object of the present invention is to provide functional immunocytes capable of activating innate immunity and a method for producing the immunocytes, as a new tool capable of appropriately inducing the activation of immunity in the immune response in the body.

Solution to Problem

The present inventors have found that a modified immunocyte having an improved productivity of Th1 cytokines (particularly interferon-γ) through the activation by the receipt of the stimulation from a CD1d ligand can be prepared by expressing an invariant T-cell receptor of a NKT cell on a surface of a particular T cell. Further, the modified immunocyte not only has improved the productivity of Th1 cytokines through the stimulation of a CD1d ligand, but also has showed an improvement in the cell proliferation ability. No report has been made at all on what conditions should be satisfied in order to make the above specific immunocyte to be in a state of triggering appropriate immune induction as described above. As a result of intensive studies based on these findings, the present inventors have completed the present invention. That is, the present invention includes the following features in order to solve the above problems.

(1) A modified immunocyte, expressing: an exogenous invariant T-cell receptor α chain; and an exogenous T-cell receptor β chain forming a dimer with the T-cell receptor α chain, on a surface of the modified immunocyte; and (2) a modified immunocyte, including: a polynucleotide encoding an invariant T-cell receptor α chain; and a polynucleotide encoding a T-cell receptor β chain forming a dimer with the T-cell receptor α chain.

Advantageous Effects of Invention

According to the present invention, a new tool capable of appropriately inducing the activation of immunity in the immune response in the body can be provided.

DESCRIPTION OF EMBODIMENTS

Figure 1:
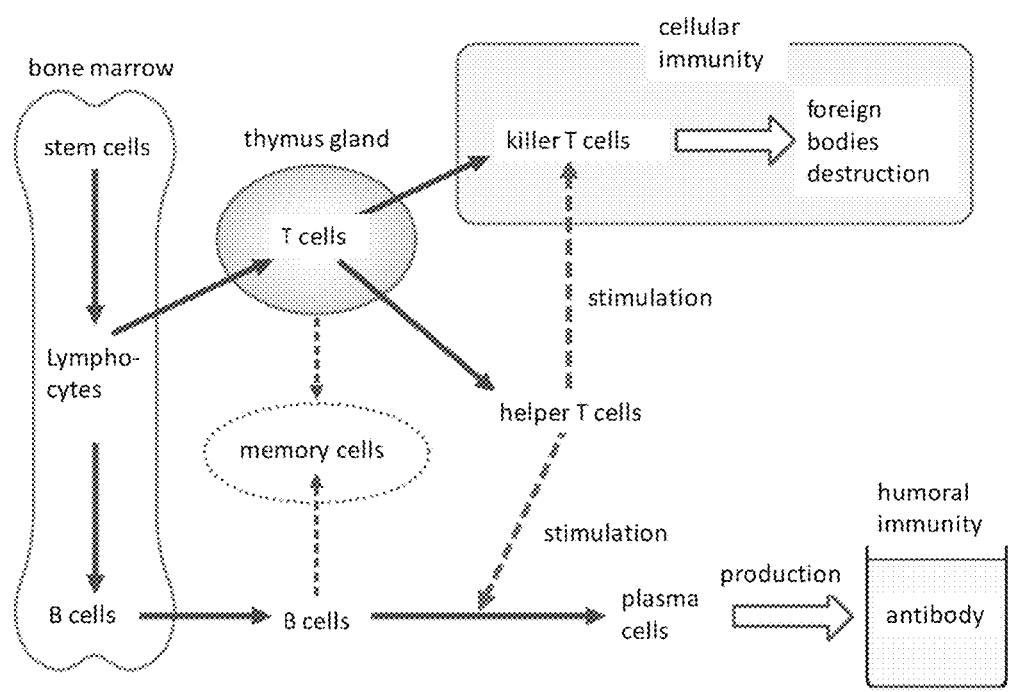
FIG. 1 is a diagram showing that modified immunocytes were able to be prepared by using T cell lines.

[Modified Immunocyte According to the Present Invention]

A first aspect of the present invention is to provide a modified immunocyte. The modified immunocyte (1) expresses an exogenous invariant T-cell receptor α chain, and an exogenous T-cell receptor β chain forming a dimer with the T-cell receptor α chain on a surface of the modified immunocyte; or (2) contains a polynucleotide encoding an invariant T-cell receptor α chain, and a polynucleotide encoding a T-cell receptor β chain forming a dimer with the T-cell receptor α chain.

The modified immunocyte effectively produces Th1-type cytokines (in more detail, induces the production of interferon-γ so as to show high yield) by the stimulation of a CD1d ligand while expressing an invariant T-cell receptor α chain and a T-cell receptor β chain on a surface of the modified immunocyte. According to the present invention, as proved in Examples, even a cell line can be used as a material, therefore, the same advantage as that of using the desired number of the functional immunocytes that enhance innate immunity can be practically received. As proved in Examples, the modified immunocyte produces interferon-γ, and when being co-cultured with a dendritic cell (DC), the modified immunocyte strongly induces the production of IL-12 (IL-12p70) almost without inducing the production of IL-10, which is the immunosuppressive, by DC. Therefore, the modified immunocytes are suitable for use in immunotherapy for improving innate immunity based on the induction of direct and indirect cytokine production.

When being used in the present specification, the term "T cell" means a T cell on which TCR of a NKT cell (hereinafter referred to as NKT-TCR) is not originally surface-expressed. That is, the α and β chains of NKT-TCR in the modified immunocyte are not endogenous but are exogenous. Therefore, when being used in the present specification, the "T cell" can be read as a "T cell other than the NKT cell". From the above, in a case of referring to a NKT cell in the present specification, "NK" or "natural killer" is necessarily added before the "T cell" to describe this.

When being used in the present specification, the "NKT cell" is a CD1d-restricted T cell. That is, in more detailed definition, the NKT cell is a cell in which the diversity to the ligand of TCR is limited, and such a NKT cell is also referred to as an invariant NKT cell (iNKT cell).

An exogenous T-cell receptor (hereinafter referred to as TCR) α chain expressed on a surface of a modified immunocyte is an α chain (for example, human Vα24 and mouse Vα14) specific to an iNKT cell. An exogenous TCR β chain expressed on a surface of a modified immunocyte is a β chain (for example, human Vβ11, and mouse Vβ8.2, Vβ7 and Vβ2) specific to an iNKT cell, which forms a dimer with the TCR α chain as described above. Further, in the modified immunocyte, in a case of using a T cell derived from human, it is preferred that the TCR α chain is Vα24, and the TCR β chain is Vβ11.

In one embodiment of the T-cell receptor to be used in the present invention, for example, human Vα24 is encoded by the polynucleotide represented by the nucleic acid sequence deposited under GenBank Accession No. DQ341448, and human Vβ11 is encoded by the polynucleotide represented by the nucleic acid sequence deposited under GenBank Accession No. DQ341459. In addition, as shown in Example 1, the nucleic acid sequence information of the polynucleotide encoding the invariant T-cell receptor α chain to be used in the present invention can be determined, for example, by subcloning the NKT cell lines established from healthy volunteers. In the similar way, the nucleic acid sequence information of Vα14, Vβ8.2, Vβ7, Vβ2, and the like can be determined from the NKT cell lines derived from mice. Based on the nucleic acid sequence information, the polynucleotide of the TCR α chain or TCR β chain of the present invention can be prepared.

Suitably, the polynucleotide encoding the TCR α chain to be used in the present invention is preferably a polynucleotide showing high homology with SEQ ID NO: 1, and the polynucleotide encoding the TCR β chain is preferably a polynucleotide showing high homology with SEQ ID NO: 2. Herein, the "high homology" means 90% or more of homology, preferably 95% or more of homology, and more preferably 98% or more of homology.

The cell that can be used as a material for preparing the modified immunocyte is a T cell, and preferably a CD3 positive T cell (γδ T cell, αβ T cell expressing variant TCR, mucosa-associated invariant T (MAIT) cell, and the like) (in the present specification, with the intention of CD3 positive T cell, also referred to as a Cd3 positive cell). The CD3 positive T cell is not particularly limited, but may be an established T cell line, a T cell collected from an individual, or the like. Specific examples of the CD3 positive T cell can include an activated T cell, a γδ T cell, and/or a MAIT cell. The activated T cell, γδ T cell, and/or MAIT cell may be (1) activated after being collected in an inactive state, or (2) activated at the time point when the cell is collected. Herein, in the case of (1), for example, an established inactive T cell line or an inactive T cell collected from an individual can be activated by stimulation in vitro. In the case of (2), for example, the cell is derived from the peripheral blood collected from an individual, and activated at the time of the collection. As confirmed in Example 3 described later, in the immunotherapy or immune induction in which a cell collected from an individual as a preparation material is returned to the individual as a modified immunocyte, a CD3 positive T cell derived from the peripheral blood of the individual is most preferred.

In one embodiment, the modified immunocyte is stored (preferably cryopreserved) or used while keeping the state at the time of being prepared. In another embodiment, the modified immunocyte is activated after the preparation, and then stored (preferably cryopreserved) or used. In this embodiment, the modified immunocyte is activated by a CD1d ligand or a proliferation activator of a γδ T cell. By the activation, the modified immunocyte shows the improvement in the cell proliferation ability together with the effective production of interferon-γ (Examples 1 to 3), and shows the functional maturation of a dendritic cell (DC) (Example 2).

The CD1d ligand means a glycolipid recognized by NKT-TCR in a state of being bound to CD1d. Examples of the glycolipid include α-GalCer (α-galactosylceramide), α-C-GalCer (α-C-galactosylceramide), iGB3 (isoglobotri-hexosylceramide), GD3 (ganglioside 3), GSL-1(α-linked glucuronic acid), and GSL-1' SA (galacturonic acid). Among them, α-GalCer or α-C-GalCer is preferred.

The proliferation activator of a γδ T cell is a known agent that proliferates and activates γδ T cells. Examples of the known agent include aminobisphosphonate, zoledronic acid, pamidronate disodium, (E)-4-hydroxy-3-methyl-2-butenyl diphosphate, and a heat shock protein.

In one embodiment, the activation of the modified immunocyte according to the present invention can be performed by bringing the CD1d-expressing cell in a state of being pulsed (loaded) with a CD1d ligand into contact with the modified immunocyte in a reaction system in vitro. In another embodiment, the activation may be performed by administering the modified immunocyte and the CD1d ligand-pulsed CD1d expressing cell to a subject to be administered. By the administration to a subject to be administered, the modified immunocyte and the CD1d ligand-pulsed CD1d expressing cell are brought into contact with each other in the body of the subject, and the modified immunocyte can be activated in the similar manner as in the reaction system in vitro. In this case, the CD1d-expressing cell and the modified immunocyte are administered simultaneously or sequentially to the subject to be administered. Here, in a case where the CD1d-expressing cell and the modified immunocyte are administered sequentially to the subject to be administered, the order of the administration of the two cells to the subject to be administered is not particularly limited.

The CD1d-expressing cell in a state of being pulsed (loaded) with a CD1d ligand can be obtained by binding the CD1d ligand to the CD1d on the cell surface through co-culturing of any CD1d-expressing cell with a CD1d ligand. The CD1d-expressing cell can be a tumor cell, a dendritic cell normally present in healthy subjects, or any cell expressing CD1d from a polynucleotide encoding CD1d artificially introduced (including established cell lines) (for example, see WO 2007/097370, WO 2010/061930, WO 2013/018778, and the like).

In one embodiment, the TCR α and TCR β chains are expressed via a vector introduced into the modified immunocyte. In this embodiment, in a case where the vector is the mRNA itself, the TCR α and TCR β chains are translated directly from the mRNAs. In this embodiment, the modified immunocyte maintains the expression of the TCR α and TCR β chains over at least around 48 hours after the introduction of mRNAs. Therefore, it is preferred that the modified immunocyte in this embodiment is used within at least around 48 hours after the preparation, after being activated by the above-described CD1d ligand and/or a proliferation activator of a γδ T cell (except in a case where the modified immunocyte is stored (preferably cryopreserved)). This is because the modified immunocyte in this embodiment returns to the original state of the body as the degradation of mRNAs, and does not express the TCR α and TCR β chains. That is, the immunotherapy and the immune induction in the body, in which the modified immunocyte in this embodiment is used, do not fall under gene therapy.

In one embodiment, the TCR α and TCR β chains are expressed from the DNA maintained in the modified immunocyte. The modified immunocyte in this embodiment is activated at an appropriate time point before use. Therefore, in this embodiment, the modified immunocyte can be stably and easily proliferated to the required number of cells by culturing.

The modified immunocyte in one aspect of the present invention is suitable for a cell for immunotherapy, an immunity inducer described later, and various other applications.

As described above, the modified immunocyte in one aspect of the present invention is suitable as a cell for immunotherapy. Examples of the disease that can be treated by the modified immunocyte include, but are not limited to, cancers, infections, and allergic diseases. Further, the modified immunocyte can be used in combination with other cells for immunotherapy. In particular, the modified immunocyte can be used together with the cell to be functional and to be activated as a result of the above-described production of interferon-γ, functional maturation of DCs, and the like. Herein, treatment has been described as an example, but the modified immunocyte in one aspect of the present invention is effective for preventing the above-described diseases by inducing the immunity in an individual.

[Immunity Inducer According to the Present Invention]

A second aspect of the present invention is to provide an immunity inducer containing the modified immunocyte. This modified immunocyte can induce an immune response in an individual according to the production of interferon-γ, the maturation of DCs, and the like. Although the modified immunocyte can exhibit immune inducibility by activation, activation of the modified immunocyte can be implemented inside or outside of the body.

Therefore, in one embodiment, the immunity inducer further contains an activator for the modified immunocyte. The activator is specifically described as the CD1d ligand and the proliferation activator of a γδ T cell as described above. In another embodiment, the immunity inducer is made into a kit by combining with the activator.

Further, in another embodiment, the immunity inducer is made into a kit by combining with a CD1d ligand-pulsed CD1d-expressing cell. In this embodiment, the CD1d ligand-pulsed CD1d-expressing cell can be administered at the same time as or before and after the administration of the immunity inducer.

[Method for Producing Modified Immunocyte According to the Present Invention]

A third aspect of the present invention is to provide a method for producing the above-described modified immunocyte. The method includes introducing a polynucleotide encoding an invariant T-cell receptor α chain, and a polynucleotide encoding a T-cell receptor β chain forming a dimer with the T-cell receptor α chain, into a CD3 positive cell.

In one embodiment, the coding region in each of the two polynucleotides is formed by RNA. That is, a preferable example of the polynucleotide is mRNA. The main advantage of introducing mRNA into a cell is that, as described above, the method of administering the prepared modified immunocyte does not fall under gene therapy.

In another embodiment, the coding region in each of the two polynucleotides can be formed by DNA capable of persistently transforming cells. Accordingly, as an example of the polynucleotide, a known vector or the like in which a polynucleotide encoding a T-cell receptor α chain and a polynucleotide encoding a T-cell receptor β chain are contained can be mentioned.

In one embodiment, the CD3 positive cell is derived from peripheral blood. The peripheral blood is preferably obtained from a subject to whom the modified immunocyte is to be administered. In an embodiment in which the CD3 positive cell is a γδ T cell, the CD3 positive cell can be proliferated by the proliferation activator of a γδ T cell before the introduction of the two polynucleotides. As described in Examples below, the γδ T cell proliferates by a treatment using a proliferation activator. Therefore, the initial existing number of the γδ T cells in peripheral blood can be secured at least in a sufficient number of γδ T cells.

[Method for Activating Modified Immunocyte According to the Present Invention]

A fourth aspect of the present invention is to provide a method for activating a modified immunocyte. The method includes co-culturing a modified immunocyte with a CD1d ligand or a proliferation activator of a γδ T cell. Details of the modified immunocyte, the CD1d ligand, and the proliferation activator of a γδ T cell are all as described in the previous items.

In a preferred embodiment, the CD1d ligand is bound to CD1d. In some embodiments, a CD1d ligand is bound to the CD1d expressed on a surface of a dendritic cell. In a specific embodiment, the dendritic cell is a human dendritic cell into which a polynucleotide encoding a disease-specific antigen has been introduced. This is because the antigenic peptide can further induce the acquired immunity in the body of a subject. In another embodiment, a CD1d ligand is bound to immobilized CD1d. In this case, the modified immunocyte can be used for administration to a subject without the isolation of the activated modified immunocyte.

SUMMARY

To summarize the above, the present invention includes the following features in order to solve the above problems.
(1) A modified immunocyte, expressing an exogenous invariant T-cell receptor α chain, and an exogenous T-cell receptor β chain forming a dimer with the T-cell receptor α chain, on a surface of the modified immunocyte;
(2) A modified immunocyte, including a polynucleotide encoding an invariant T-cell receptor α chain, and a polynucleotide encoding a T-cell receptor β chain forming a dimer with the T-cell receptor α chain;
(3) The modified immunocyte described in the above (1) or (2), in which the invariant T-cell receptor α chain is Vα24, and the T-cell receptor β chain is Vβ11;
(4) The modified immunocyte described in any one of the above (1) to (3), in which (i) a variant T-cell receptor α chain and a T-cell receptor β chain, or (ii) a T-cell receptor γ chain and a T-cell receptor δ chain are further expressed on a surface of the modified immunocyte;
(5) The modified immunocyte described in the above (4), in which a cell being a material for the modified immunocyte is a γδ T cell derived from peripheral blood;
(6) The modified immunocyte described in any one of the above (1) to (5), activated by a CD1d ligand and/or a proliferation activator of a γδ T cell;
(7) An immunity inducer, containing the modified immunocyte described in any one of the above (1) to (6);
(8) The immunity inducer described in the above (7), further containing a CD1d ligand and/or a proliferation activator of a γδ T cell;
(9) A method for producing a modified immunocyte, including introducing a polynucleotide encoding an invariant T-cell receptor α chain, and a polynucleotide encoding a T-cell receptor β chain forming a dimer with the T-cell receptor α chain, into a CD3 positive cell;
(10) The method described in the above (9), in which a coding region in each of the two polynucleotides is formed by RNA;
(11) The method described in the above (10), in which a material for the modified immunocyte is collected from peripheral blood or a sample obtained by culturing the peripheral blood;
(12) A method for activating a modified immunocyte, including co-culturing a modified immunocyte produced by the method described in any one of the above (9) to (11) with a CD1d ligand and/or a proliferation activator of a γδ T cell;
(13) The method described in the above (12), in which the CD1d ligand is bound to CD1d; and
(14) A method for inducing immunity of a subject, including administering the modified immunocyte described in any one of the above (1) to (6) or the immunity inducer described in the above (7) or (8) to the subject.

EXAMPLES

[Materials and Methods]

Materials and methods used in each of the Examples described later are as follows.

(Reagents)

Human and canine recombinant GM-CSF and IL-4 were purchased from R&D systems (Minneapolis, MN). IL-2 was purchased from Shionogi & Co., LTD (Osaka, Japan). α-GalCer was synthesized by Dr. Yasuyuki Ishii in RIKEN. α-GalCer and vehicle (0.4% dimethylsulfoxide (DMSO)) were diluted in phosphate-buffered saline (PBS). Zoledronic acid (ZOL) was purchased from Novartis Pharmaceuticals Ltd. The following monoclonal antibodies (mAbs) were purchased, respectively: anti-human CD3, anti-human CD11c (B-ly6), anti-human CD40, anti-human CD86 (2311), and an associated receptor of a α chain and a β chain of human invariant NKT cells (6B11) from BD (San Diego, CA); anti-human Vα24 (C15), Vβ11 (C21), γ9 from Beckman Coulter; anti-human CD3 (UCHT1) from e-Bioscience; and anti-human CD1d-tetramer from MBL. A FACS Calibur (trademark) instrument and CELLQuest (trademark) software (BD Biosciences) or FlowJo (Tree Star, San Carlos, CA) software were used for analysis.

(Cell Lines)

A Jurkat cell line was obtained from BRC, RIKEN. A HEK293 cell line was purchased from the American Type Culture Collection (Rockville, MD). In order to introduce human CD1d into HEK293 cells, pCMV6-XLA4/hCD1d (OriGene Technologies Inc., Rockville, MD) and a pCAG-puromycin resistance gene (provided by Dr. Keigo Nishida in RCAI, RIKEN) were co-transfected into HEK293 cells, and the resultant cells were selected by puromycin. After one week, MX-hCD1d-transfected HEK293 cells were subsequently sorted based on the expression of hCD1d by FACS Aria Sorter.

(Isolation of Human PBMC)

Human PBMCs were obtained from buffy coats derived from healthy blood donors, and isolated by density gradient centrifugation of Ficoll-Hypaque (Amersham Pharmacia Biotech, Uppsala, Sweden). In a case of PBMCs and in some cases, CD14$^+$ monocytes purified by magnetic beads (Miltenyi Biotec Inc.) separation were washed three times with PBS, and the resultant CD14$^+$ monocytes were stored using a serum-free cryopreservation medium Cellbanker 2 (JUJI Field Inc., Tokyo, Japan) in liquid nitrogen until use. All of the tests were approved by the RIKEN institutional review board.

(Generation of Human Dendritic Cells (DCs))

CD14$^+$ cells isolated by using magnetic beads (Miltenyi Biotec Inc.) were used for the generation of immature DCs (imDCs). Monocytes were cultured for 3 days in the presence of GM-CSF (100 ng/mL) and IL-4 (25 ng/mL) to generate imDCs.

(In Vitro Generation of iNKT Cell Lines and Vγ9Vδ2 T Cell Lines)

In order to prepare NKT cell lines, PBMCs were pulsed using α-GalCer (100 ng/mL) in the presence of 100 U/mL IL-2. After 10 to 14 days, human iNKT cells were stained using FITC-labeled anti-VαmAb, and selected using anti-FITC magnetic beads (Miltenyi Biotec Inc.). Human iNKT cells were maintained in the presence of 100 U/mL IL-2, 5 ng/mL IL-7, and 10 ng/mL IL-15.

In order to prepare Vγ9Vδ2 T cell lines, PBMCs were cultured in the presence of ZOL (100 μmol/L) and 300 U/mL IL-2. After 10 to 14 days, γδ T cells were stained using FITC-labeled anti-γ9mAb, and selected using anti-FITC magnetic beads (Miltenyi Biotec Inc.). Human Vγ9Vδ2 T cells were maintained in the presence of 300 U/mL IL-2.

(In Vitro Transcription (IVT) of RNAs)

EGFP (enhanced green fluorescent protein) in a pSP64 Poly (A) vector was excised with HindIII and BamHI, and re-cloned into a pGEM-4Z vector (Promega, Madison, WI). The ovalbumin (OVA) plasmid used for this test has been previously described. The expression plasmid for MART-1 (pcDNA3 (+)-MART-1) was isolated. For the IVT, these plasmids were linearized by restriction enzyme digestion (BamHI for EGFP and OVA, and NotI for MART-1), purified by a QIAquick PCR Purification Kit (QIAGEN GmbH, Hilden, Germany), and used as a template. The RNAs were generated under the control of a T7 promoter sequence on the vector by using a mMESSAGE mMACHINE T7 Ultra Kit (Ambion, Austin, TX). The template DNAs were digested with DNase I based on the kit. IVT RNAs were then purified by an RNeasy Mini/Midi Kit (QIAGEN, Valencia, CA), and eluted in water. RNA integrity was verified by agarose gel electrophoresis under denaturing conditions, and the concentration was determined by a spectrophotometer.

(Preparation of TCR-Transduced PBLs)

RNA electroporation of T cells was performed as reported so far. In brief, peripheral blood leukocytes (PBLs) at $10^6$ cells/mL were stimulated in vitro with 50 ng/mL anti-CD3 mAb OKT3 (Janssen pharmaceutical, Inc., Tokyo, Japan) and 300 IU/mL IL-2 in 10% FCS-containing RPMI. Two or three days later, T cells were washed once with OptiMEM, and suspended in OptiMEM at a concentration of $5 \times 10^6/100$ μL. 10 μg of each RNA was transferred to a 4-mm cuvette, 100 μL of cell suspension was added into the cuvette, and the resultant mixture was pulsed in a BTX. The pulse conditions were square-wave pulse, 500 V, and 5 m second. Immediately after the electroporation, the cells were transferred to a fresh CM with 300 IU/mL IL-2, and incubated at 37° C.

(Cytokine Production Assay)

After the electroporation of NKT-TCR mRNA, Vα24$^+$ Vβ11$^+$ cells and Vα24$^-$Vβ11$^-$ cells were sorted by FACS Aria, and used as responder cells. For a stimulator, CD1d 293 was pulsed for 24 hours with or without 500 ng/mL α-GalCer. In some experiments, CD1d 293 was treated for 24 hours with 10 μmol/L ZOL, and used as a stimulator. $1 \times 10^5$ responder cells were co-cultured for 24 hours with $1 \times 10^4$ stimulator cells. The culture supernatant was harvested, and interferon-γ production was measured by IFN-γ ELISA (BD).

(DC Maturation)

NKT-TCR mRNA-electroporated T cells were sorted, and then co-cultured with autologous immature DCs (1:1) for 24 hours in the presence or absence of 100 ng/mL α-GalCer. As a positive control, 100 ng/mL LPS were used. After 24 hours, DCs were analyzed for CD40 and CD86 by flow cytometry, and IL10 and IL12 p70 production in the culture supernatant was measured by ELISA (BD).

(Cytotoxicity Assay)

The cytotoxic activity of γδ T cells or NKT-TCR-electroporated γδ T cells were analyzed by using a LDH assay kit according to instructions of the manufacturer (Takara Bio Company). As target cells, CD1d 293 was treated for 24 hours with or without 500 ng/mL α-GalCer or 10 μmol/L ZOL. $1 \times 10^4$ target cells were co-cultured with $10 \times 10^5$ effector cells for 12 hours in 1% FCS/RPMI. The culture supernatant was incubated with a freshly prepared Reaction Mixture containing tetrazolium salts, and the absorbance was measured at 490 nm. The data are mean±standard deviation of triplicate wells based on three independent experiments. After subtracting the background control value, the cytotoxicity value (%) was calculated as follows. Cytotoxicity (%)={(effector: target cell mixture−effector cell control)−spontaneous target cell control}/(maximum target cell control−spontaneous target cell control)×100

(Statistical Analysis)

Differences in the in vitro data were analyzed using a Mann-Whitney U test. $P<0.05$ was considered statistically significant.

Example 1: Preparation of Modified Immunocytes Using Jurkat Cell Lines

Vα and Vβ chains of NKT cell TCR derived from the NKT cell lines that had been established from healthy volunteers were initially subcloned. The mRNAs were generated from the coding regions of TCR α and TCR β chains in the DNA (TCR α chain: SEQ ID NO: 1, and TCR β chain: SEQ ID NO: 2), respectively by an in vitro transcription approach. After both of the TCR chains were transfected into Jurkat T cells by electroporation, the expression of NKT-TCR was determined by cytometry using a combination of anti-Vα24 and Vβ11 Ab, or a combination of CD3 and anti-6B11 or anti-CD1d/Gal-tetramer (FIG. 1A).

As reported, an expression of both of the Vα24 and Vβ11 was evaluated by anti-6B11 mAb. The expression level of NKT-TCR was up-regulated during 6 to 12 hours, and decreased 48 hours later (FIG. 1B). Particularly, the expression of the Vα24 and Vβ11 was detected on the Jurkat cells exceeding 90% of the whole Jurkat cells after 6 hours. After that, the downstream of the TCR signal was assessed after the cells were cultured together with a solid phase of α-GalCer-binding CD1d antibody. Mitogen-activated protein kinase (MAPK) was phosphorylated in 10 minutes after the stimulation (FIG. 1C), and it is indicated that TCR signaling was clearly augmented in the Vα24 and Vβ11 TCR mRNA-transfected Jurkat cells.

As described above, by introducing the mRNAs of the TCR α and TCR β chains, a modified immunocyte transiently expressing functional NKT-TCR on a Jurkat cell was able to be produced.

Figure 2:
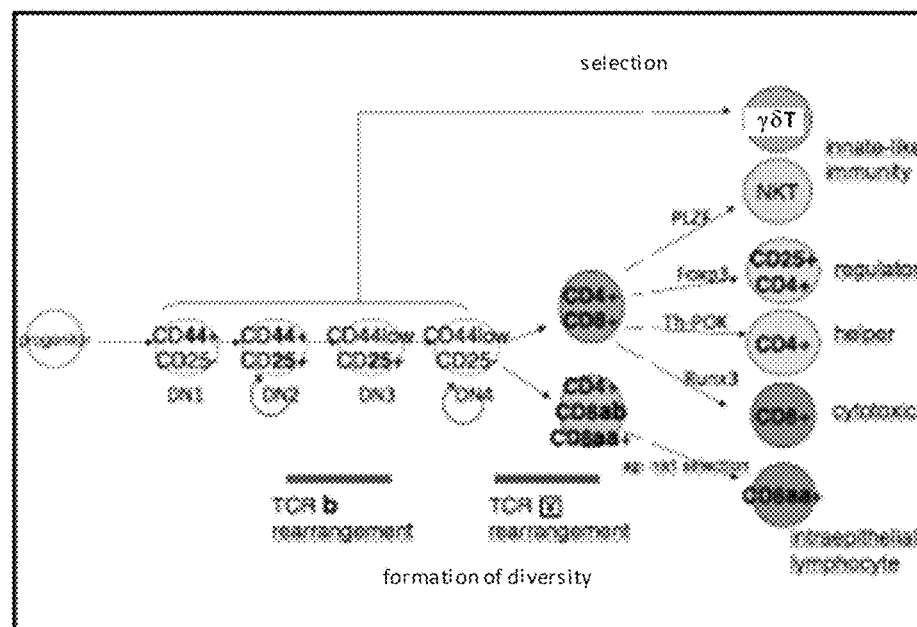
FIG. 2 is a diagram in which modified immunocytes prepared by using activated T cells derived from peripheral blood mononuclear cells (PBMCs) and the cytokine productivity thereof were confirmed.

Example 2: Preparation of Modified Immunocytes Using Activated T Cells Derived from Peripheral Blood Mononuclear Cells (PBMCs) of Healthy Subjects The mRNAs of Vα24 and Vβ11 TCR chains were transfected into an activated primary T cell that had been generated for 3 days by anti-CD3 Ab and IL-2. The expression of TCR α chain (Vα24) and β chain (Vβ11) on the mRNA-transfected T cell was assessed by anti-6B11 mAb. The 6B11$^+$ cells were 60 to 70% of the cells derived from CD3$^+$ T cells, and it is indicated that both of the chains were apparently expressed on the surfaces of the cells (FIGS. 2A and 2B).

The TCR signaling was analyzed in Vα24$^+$Vβ11$^+$ transfected (hereinafter referred to as "NKT-TCR$^+$") cells and Vα24$^-$Vβ11$^-$ non-transfected (hereinafter referred to as "NKT-TCR$^-$") cells after the stimulation with a solid phase of α-GalCer-binding CD1d antibody. The NKT-TCR$^+$ cells, but not the NKT-TCR$^-$ cells showed the activation of MAP kinase signal (right column of FIG. 2C).

Furthermore, the cytokine production was analyzed by co-culturing the NKT-TCR$^+$ cells together with the cells loaded with α-GalCer (CD1d-HEK293 cells/Gal). The NKT-TCR$^+$ cells produced more interferon-γ but not IL-4 in a α-GalCer dependent manner. However, both of the NKT-TCR$^-$ cells and the activated T cells without transfection did not produce any interferon-γ (FIG. 2D). Therefore, the Vα24 TCR and Vβ11 TCR mRNA-transfected activated T cells (NKT-TCR$^+$ cells) were functional to produce interferon-γ, and it is indicated that these Th1 type-skewed 6B11$^+$ cells can mimic Th1 type NKT cells for 48 hours.

Subsequently, the adjuvant effect of NKT-TCR$^+$ cells was confirmed. It has been reported that NKT cells induce the maturation of DCs in both of the phenotype and function in vivo and in vitro. It was assessed whether or not the NKT-TCR$^+$ T cells can mature DCs. The maturation markers and cytokine productions were evaluated after the NKT-TCR$^+$ T cells and autologous monocyte-derived mature DCs were cultured.

Figure 3:
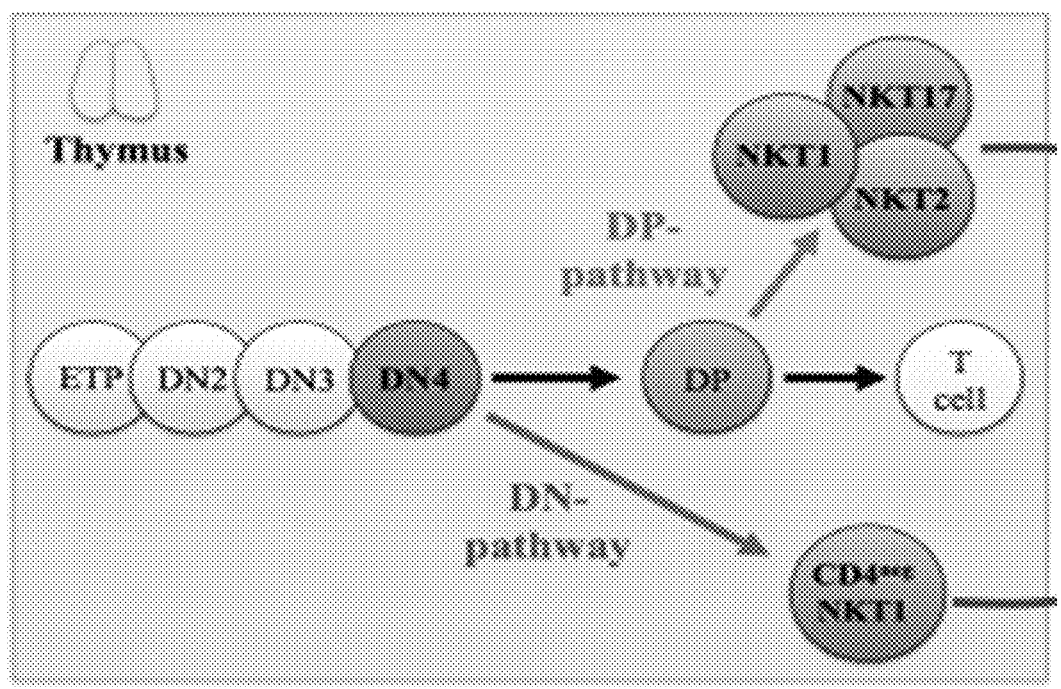
FIG. 3 is a diagram showing that the modified immunocytes in FIG. 2 can mature dendritic cells.

Up-regulation of costimulatory molecules on DCs by NKT-TCR$^+$ T cells was observed similar to the up-regulation by LPS stimulation (FIG. 3A). Further, in the DCs matured by NKT-TCR$^+$ T cells, IL-12p70 production was antigen-specifically remarkably observed, but IL-10 production was hardly observed (FIG. 3B). The L-12p70 acts in a direction of stimulating the immunity, and the IL-10 acts conversely in a direction of suppressing the immunity. Therefore, the maturation of DCs by NKT-TCR$^+$ T cells is much more favorable than the LPS stimulation for the immune induction.

Figure 4:
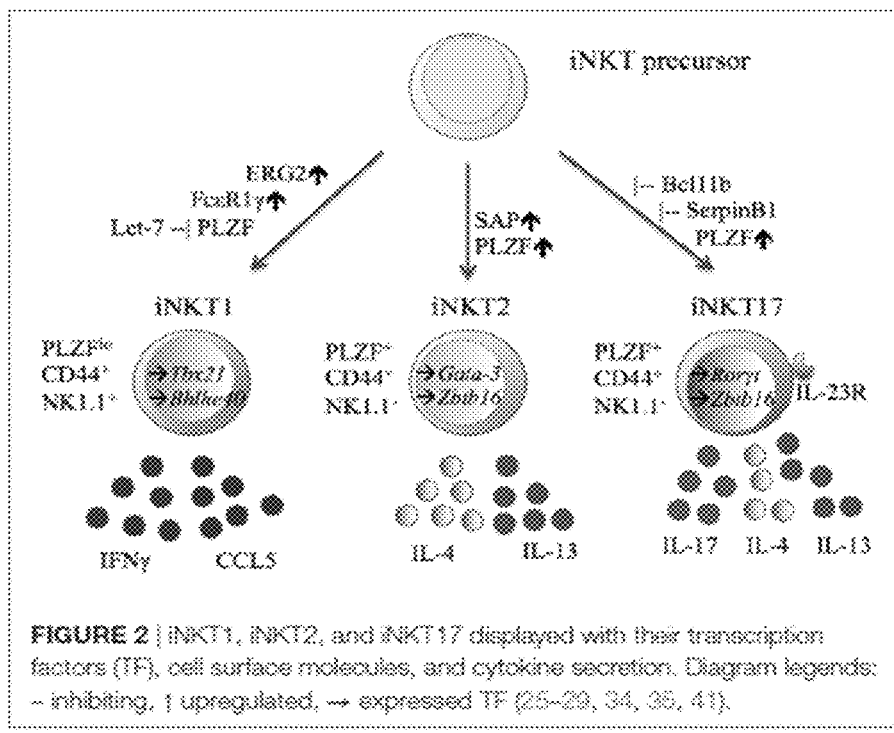
FIG. 4 is a diagram in which NKT cells and γδ T cells in peripheral blood of a healthy subject were confirmed before and after the activation by each ligand.

Example 3: Preparation of Modified Immunocytes Using γδ T Cells Derived from Peripheral Blood Mononuclear Cells (PBMCs) of Healthy Subjects The γδ T cell is well-known as one of the innate lymphocytes. Among the γδ T cells, γ9 type of γδ T cells can be proliferated by zoledronic acid (ZA)-loaded cells in which some endogenous γδ T cell ligands were up-regulated on antigen-presenting cells (APCs). As shown in FIG. 4, even those who recognize NKT cells with only extremely low frequency in the peripheral blood have the appropriate number of γδ T cells. In addition, γδ T cells have the potential to proliferate in an amount much larger than the NKT cells (FIGS. 4A and 4B).

Figure 5:
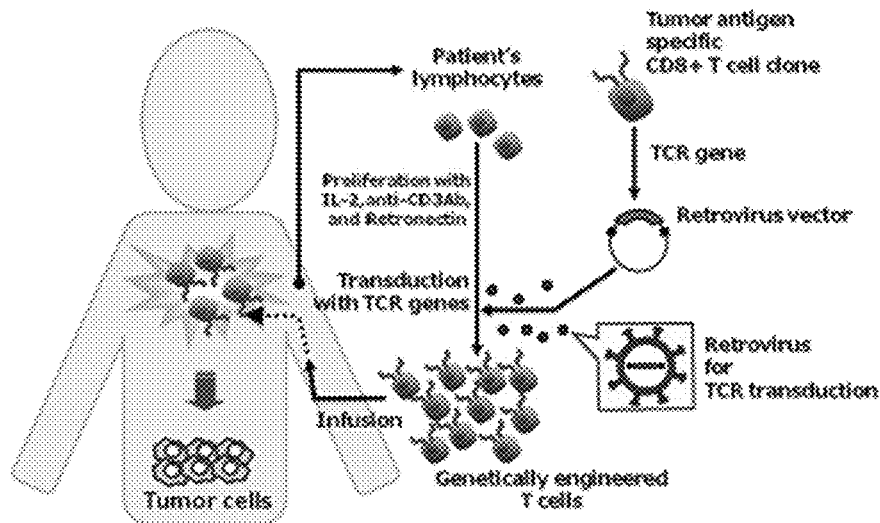
FIG. 5 is a diagram in which modified immunocytes prepared by using γδ T cells derived from PBMCs were confirmed.

Apparently, γδ T cells usually do not express NKT-TCR, however these can express NKT-TCR together with γ9δ TCR after the transfection by electroporation (FIG. 5). When these NKT-TCR$^+$ cells were co-cultured with ZA-loaded CD1d-HEK293 cells, γδ T cells produced interferon-γ, and these were confirmed to be γδ T cells.

Figure 6:
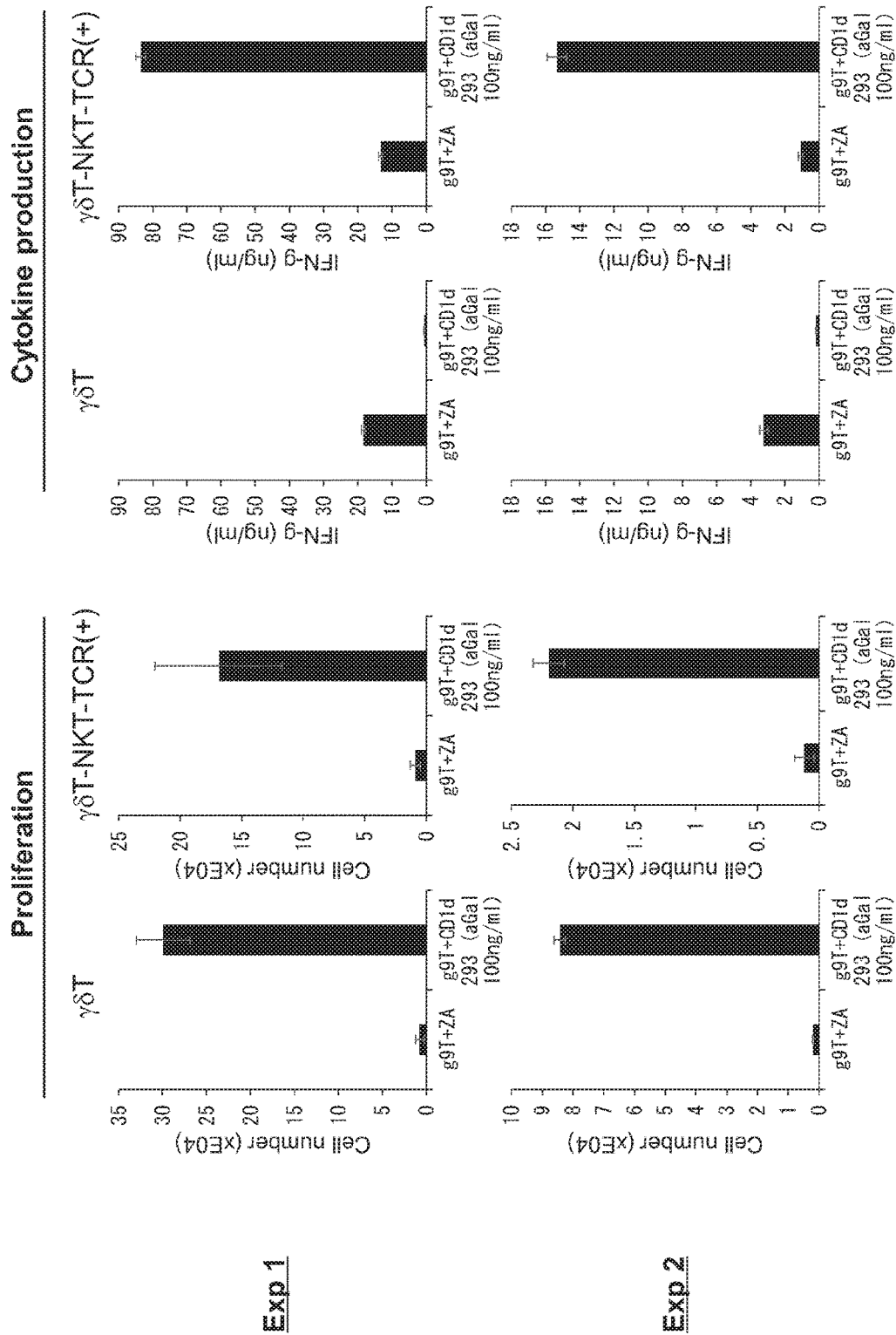
FIG. 6 is a diagram in which proliferation activation ability and cytokine productivity of the modified immunocytes in FIG. 5 were confirmed.

In order to investigate the difference in the function due to the expression of NKT-TCR in the γδ T cell, (1) the γδ T cells cultured with the stimulation of ZA, and (2) the NKT-TCR$^+$ γδ T cells co-cultured with the CD1d-HEK293 cell/Gal were compared to each other. The results are shown in FIG. 6. When the number of cells was counted in 72 hours after the stimulation or co-culture, there was a remarkable difference in the cell proliferation (left panel of FIG. 6). In the similar manner, when the yield of interferon-γ in 48 hours after the stimulation or co-culture was measured by ELISA, a remarkable increase in the yield in NKT-TCR$^+$ γδ T cells was observed (right panel of FIG. 6).

As described above, by expressing the NKT-TCR, and applying the stimulation of α-GalCer, it was indicated that the cell proliferation ability of the γδ T cells and the yield of the interferon-γ were improved.

From the above, it was found that by modifying the γδ T cells that are present in a relatively large amount in peripheral blood, and further can be proliferated in an amount sufficient for clinical use, the availability of the γδ T cells can be significantly improved. Further, based on the individual difference, the γδ T cells either are not activated by ZA alone, or cause the case where the stimulation is insufficient, but the modified γδ T cells newly bring an option to use the α-GalCer. Accordingly, the modified γδ T cells substantially reduce the number of the individuals who cannot use the γδ T cells or have low effectiveness in using the γδ T cells, and thus can provide an opportunity for the treatment to more individuals.

In addition, in common in each of the Examples described above, what has been introduced into each cell is mRNAs of the α and β chains of the NKT cell TCR. As is extremely well proved in Examples 1 and 2, the α and β chains in a cell surface decreases with the lapse of time. However, it is not that the number of cells is decreased. That is, in the NKT-TCR$^+$ cells, by the decomposition of the introduced mRNAs, the expression level of the α and β chains of the NKT cell TCR is gradually decreased, and it is eventually only returned to the state before the introduction of mRNAs. Therefore, the application of the cells obtained in these Examples to immunotherapy does not fall under the gene therapy. It is apparent that the cells of these Examples, in which the exogenous factors to be introduced do not remain, exhibit only extremely low side effects that are beyond comparison with the conventional gene therapy. In a case where the cells of these Examples are applied in the immunocyte therapy in which autologous cells are used, it can be regarded that there are substantially no side effects.

Further, the regulations for performing gene therapy are not applied, therefore, there is almost no restriction on the place to handle the cells of these Examples. Since the nature of the cells returns to the state in the body with the lapse of time, the instruments and biologically-derived materials used for preparing the cells can be disposed by a disposal method equivalent to that for the instruments and the like used usually in medical facilities.

Example 4: Confirmation of In Vivo Anti-Tumor Effect of Modified Immunocytes

In order to investigate the in vivo anti-tumor effect by immunocytes in which NKT-TCR had newly expressed, verification was performed by using a γδ T cell in which NKT-TCR had expressed (NKT-TCR$^+$ γδ T cell of Example 3: hereinafter referred to as a modified immunocyte).

Immunodeficient mice to which 2×10$^6$ K562 cells had been subcutaneously inoculated were prepared as model animals to evaluate the anti-tumor effect by the modified immunocytes. The modified immunocytes were prepared in accordance with the same procedures as those in Example 3. The following two kinds of treated products were administered to the tumor inoculation sites in the model animals in 7 days after the inoculation (respectively n=2).

Figure 7:
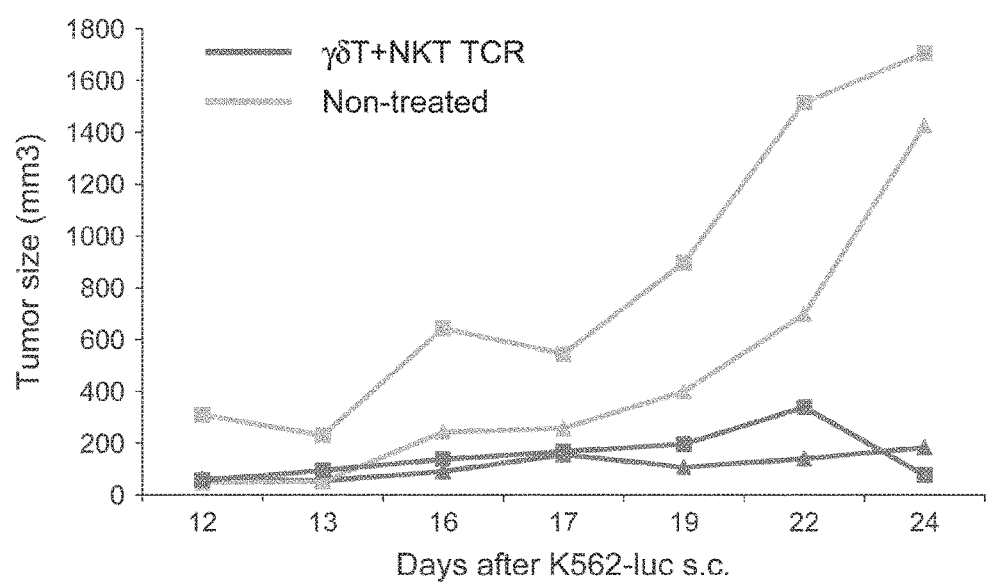
FIG. 7 is a diagram showing the results of the evaluation of the anti-tumor effects by modified immunocytes based on the tumor sizes in model animals, which had been measured in 12 to 24 days after the inoculation of tumor cells.

(1) 100 μl of medium in which 2×10⁶ modified immunocytes are suspended ("γδ+NKT TCR" in FIG. 7: dark line)
(2) 100 μl of medium alone ("non-treated" in FIG. 7: pale line)

The results of evaluating the anti-tumor effects by the modified immunocytes based on the tumor sizes in the model animals, which had been measured in 12 to 24 days after the inoculation, are shown in FIG. 7. As shown in FIG. 7, all of the model animals to which modified immunocytes had been administered showed no increase in the tumor size in 12 to 24 days after the inoculation. On the other hand, all of the model animals to which the modified immunocytes had not been administered showed increase in the tumor size with the lapse of time (in particular, after the 17th day of the inoculation). From the above, it was revealed that the modified immunocytes (NKT-TCR⁺ γδ T cells) exhibit extremely excellent anti-tumor activity in vivo.

Comparative Example: Efficacy of NK Cells Introduced with NKT-TCR

Even in a case where NKT-TCR was introduced into a NK cell, in order to investigate whether or not the same effect as that of the modified immunocyte in Example 3 is shown, the peripheral blood mononuclear cells (PBMCs) of healthy subjects, which had been collected as described above, were cultured in a medium containing 1000 U/ml IL2. After confirming the proliferation of the cells, the mRNAs for the expression of NKT-TCR were introduced into the cells, and the cell population in which NKT-TCRs were surface-expressed was confirmed. The results of the confirmation of cell proliferation and cell population by flow cytometry after the lapse of a predetermined number of days from the culture of peripheral blood mononuclear cells (PBMCs) are shown in FIG. 8.

Figure 8:
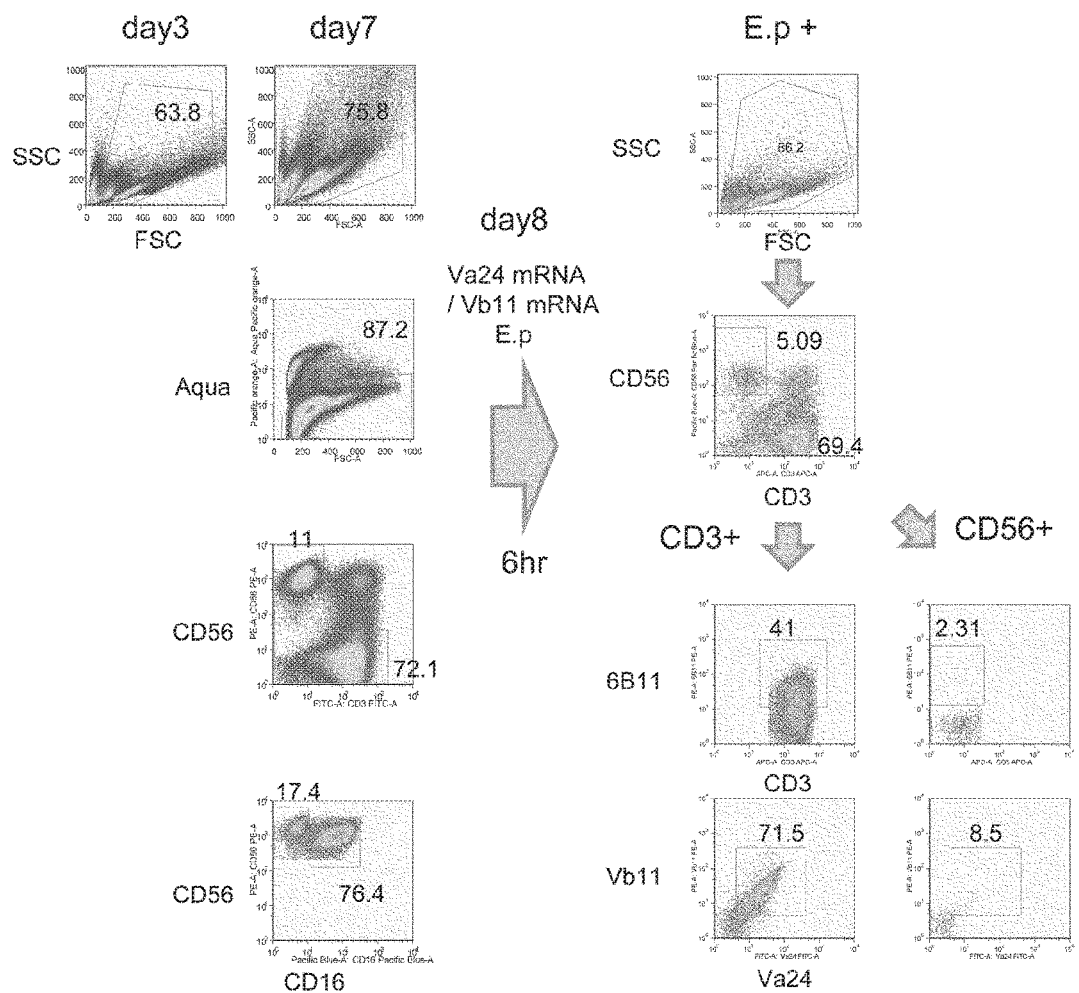
FIG. 8 is a diagram showing the results of the confirmation of cell proliferation and cell population by flow cytometry after the lapse of a predetermined number of days from the culture of peripheral blood mononuclear cells (PBMCs).

As shown on the left side of the arrow in FIG. 8, the proliferation of cells at each time point of 3 days and 7 days after the start of the culture was confirmed by flow cytometry. Further, at the time point after 7 days, the proliferation of cells was further analyzed by using other fluorescent-labeled antibodies, and CD3⁺CD56⁻ cell population (11.0%), CD3⁻CD56⁺ cell population (72.1%), CD16⁺CD56⁻ cell population (76.4%), and CD16⁻CD56⁺ cell population (17.4%) were confirmed to be present. NKT-TCR mRNAs (Vα24 RNA and Vβ11 mRNA) were electroporated at the time point of 8 days after the start of the culture, and after 6 hours, Vα24⁺Vβ11⁺ cells were confirmed by flow cytometry. As shown on the right side of the arrow in FIG. 8, the percentage of the cells reacting with anti-6B11 mAb was 41.0%, and the percentage of the Vα24⁺Vβ11⁺ cells was 71.5% in CD3⁺ cells, but on the contrary, the percentage of the cells reacting with anti-6B11 mAb was 2.31%, and the percentage of the Vα24⁺Vβ11⁺ cells was 8.5% in the CD56⁺ cells containing NK cells.

As described above, as compared with the CD3⁺ cells, in the NK cells, expression itself of the NKT-TCR was suppressed. Therefore, it was revealed that the cells that exhibit the same effects as those of the modified immunocytes based on CD3⁺ cells as prepared in Example 3 were able to be obtained only extremely inefficiently when the NK cells were used as the material. In the experiments described above, extremely unexpected results that betray usual expectation for those skilled in the art, which is the expectation that cells showing the function as in NKT cells will be obtained when the mRNAs of NKT-TCR were introduced into the NK cells, were shown. Therefore, as shown in Example 3, it has revealed that CD3⁺ cells are extremely suitable for the preparation of the modified immunocytes for immunotherapy.

The present invention is not limited to each of the above-described embodiments and Examples, and various modifications can be made within the scope indicated in the claims, and embodiments obtained by appropriately combining the technical means disclosed in different embodiments, respectively are also included in the technical scope of the present invention. Further, by combining the technical means disclosed in each embodiment and each Example, respectively, new technical features can be formed.

INDUSTRIAL APPLICABILITY

The present invention can be used for immunocyte therapy. In particular, the present invention can be used as an immunity inducer that activates the effector cells directly exhibiting cytotoxic immunity and other immunocytes.

The invention claimed is:

1. A method for producing a modified immunocyte, comprising
introducing into a human CD3 positive T cell that expresses a variant T-cell receptor α chain and a T-cell receptor β chain,
a polynucleotide encoding an exogenous Vα24, and
a polynucleotide encoding an exogenous Vβ11,
wherein each of the two polynucleotides is formed by mRNA, and
wherein said method is performed in vitro.

2. The method according to claim 1, wherein
the human CD3 positive T cell is collected from peripheral blood or a sample obtained by culturing the peripheral blood.

3. A method for activating a modified immunocyte, comprising
co-culturing a modified immunocyte produced by the method according to claim 1 together with a CD1d ligand.

4. The method according to claim 3, wherein
the CD1d ligand is bound to CD1d.

5. A modified immunocyte, expressing:
an exogenous Vα24; and
an exogenous Vβ11,
on a surface of the modified immunocyte,
wherein the modified immunocyte is produced according to the method of claim 1.

6. The modified immunocyte according to claim 5, wherein
the modified immunocyte is activated by a CD1d ligand.

7. An immunity inducer, comprising
the modified immunocyte according to claim 5.

8. The immunity inducer according to claim 7, further comprising a CD1d ligand.

9. A modified immunocyte, comprising:
a mRNA encoding an exogenous Vα24; and
a mRNA encoding an exogenous Vβ11,
wherein the modified immunocyte is produced according to the method of claim 1.

10. The modified immunocyte according to claim 9, wherein
the modified immunocyte is activated by a CD1d ligand.

11. An immunity inducer, comprising
the modified immunocyte according to claim 9.

12. The immunity inducer according to claim 11, further comprising
a CD1d ligand.

* * * * *

SEQUENCE LISTING

```
<160> NUMBER OF SEQ ID NOS: 2

<210> SEQ ID NO 1
<211> LENGTH: 831
<212> TYPE: DNA
<213> ORGANISM: Homo sapiens

<400> SEQUENCE: 1
atgaaaaagc atctgacgac cttcttggtg attttgtggc tttatttta taggggaat      60 ggcaaaaacc aagtggagca gagtcctcag tccctgatca tcctggaggg aaagaactgc    120
actcttcaat gcaattatac agtgagcccc ttcagcaact taaggtggta taagcaagat    180
actgggagag gtcctgtttc cctgacaatc atgactttca gtgagaacac aaagtcgaac    240
ggaagatata cagcaactct ggatgcagac acaaagcaaa gctctctgca catcacagcc    300
tcccagctca gcgattcagc ctcctacatc tgtgtggtga gcgacagagg ctcaaccctg    360
gggaggctat acttggaag aggaactcag ttgactgtct ggcctgatat ccagaaccct    420
gaccctgccg tgtaccagct gagagactct aaatccagtg acaagtctgt ctgcctattc    480
```

```
accgattttg attctcaaac aaatgtgtca caaagtaagg attctgatgt gtatatcaca    540
gacaaaactg tgctagacat gaggtctatg gacttcaaga gcaacagtgc tgtggcctgg    600
agcaacaaat ctgactttgc atgtgcaaac gccttcaaca acagcattat tccagaagac    660
accttcttcc ccagcccaga aagttcctgt gatgtcaagc tggtcgagaa aagctttgaa    720
acagatacga acctaaactt tcaaaacctg tcagtgattg ggttccgaat cctcctcctg    780
aaagtggccg ggtttaatct gctcatgacg ctgcggctgt ggtccagctg a             831

<210> SEQ ID NO 2
<211> LENGTH: 933
<212> TYPE: DNA
<213> ORGANISM: Homo sapiens

<400> SEQUENCE: 2
atgactatca ggctcctctg ctacatgggc ttttattttc tggggggcagg cctcatggaa     60 gctgacatct accagacccc aagataccct gttatagggga caggaaagaa gatcactctg    120
gaatgttctc aaaccatggg ccatgacaaa atgtactggt atcaacaaga tccaggaatg    180
gaactacacc tcatccacta ttcctatgga gttaattcca cagagaaggg agatctttcc    240
tctgagtcaa cagtctccag aataaggacg gagcattttc ccctgacccct ggagtctgcc    300 aggccctcac atacctctca gtacctctgt gccagcgagc agaggggggg agtagatgaa    360
aaactgtttt ttggcagtgg aacccagctc tctgtcttgg aggacctgaa caaggtgttc    420
ccacccgagg tcgctgtgtt tgagccatca gaagcagaga tctcccacac ccaaaaggcc    480
acactggtgt gcctggccac aggcttcttc cctgaccacg tggagctgag ctggtgggtg    540
aatgggaagg aggtgcacag tggggtcagc acgaccccgc agcccctcaa ggagcagccc    600
gccctcaatg actccagata ctgcctgagc agccgcctga gggtctcggc caccttctgg    660
cagaaccccc gcaaccactt ccgctgtcaa gtccagttct acgggctctc ggagaatgac    720
gagtggaccc aggataggc caaacccgtc acccagatct cagcgccga ggcctggggt    780 agagcagact gtggctttac ctcggtgtcc taccagcaag ggtcctgtc tgccaccatc    840 ctctatgaga tcctgctagg gaaggccacc ctgtatgctg tgctggtcag cgccttgtg    900 ttgatggcca tggtcaagag aaaggatttc tga                                933
```